United States Patent [19]

Sellers

[11] Patent Number: 5,678,562
[45] Date of Patent: Oct. 21, 1997

[54] AMBULATORY PHYSIOLOGICAL MONITOR WITH REMOVABLE DISK CARTRIDGE AND WIRELESS MODEM

[75] Inventor: Craig S. Sellers, Red Creek, N.Y.

[73] Assignee: Burdick, Inc., Milton, Wis.

[21] Appl. No.: 558,703

[22] Filed: Nov. 9, 1995

[51] Int. Cl.[6] .................... A61B 5/04; A61B 5/0404; A61B 5/0432; A61B 5/044
[52] U.S. Cl. .................... 128/710; 128/696; 128/904; 128/711
[58] Field of Search .................... 128/696, 702, 128/710, 711, 903, 904

[56] References Cited

U.S. PATENT DOCUMENTS

| | | | |
|---|---|---|---|
| 3,882,277 | 5/1975 | DePedro et al. | 179/2 DP |
| 4,592,018 | 5/1986 | Wiegman | 365/63 |
| 4,974,599 | 12/1990 | Suzuki | 128/710 |
| 4,974,607 | 12/1990 | Miwa | 128/904 |
| 5,002,062 | 3/1991 | Suzuki | 128/710 |
| 5,012,411 | 4/1991 | Policastro et al. | 128/710 |
| 5,086,778 | 2/1992 | Mueller et al. | 128/710 |
| 5,113,869 | 5/1992 | Nappholz et al. | 128/696 |
| 5,153,584 | 10/1992 | Engira | 340/870.18 |
| 5,205,295 | 4/1993 | Del Mar et al. | 128/711 |
| 5,226,431 | 7/1993 | Bible et al. | 128/904 |
| 5,228,450 | 7/1993 | Sellers | 128/711 |
| 5,343,869 | 9/1994 | Pross et al. | 128/710 |
| 5,381,798 | 1/1995 | Burrows | 128/696 |
| 5,416,695 | 5/1995 | Stutman et al. | 364/413.02 |
| 5,417,222 | 5/1995 | Dempsey et al. | 128/696 |
| 5,458,123 | 10/1995 | Unger | 128/696 |
| 5,503,158 | 4/1996 | Coppock et al. | 128/710 |
| 5,522,396 | 6/1996 | Langer et al. | 128/696 |
| 5,544,661 | 8/1996 | Davis et al. | 128/700 |
| 5,606,978 | 3/1997 | Armstrong et al. | 128/696 |

FOREIGN PATENT DOCUMENTS

0 080 821  8/1983  European Pat. Off. .

*Primary Examiner*—William E. Kamm
*Assistant Examiner*—Carl H. Layno
*Attorney, Agent, or Firm*—Wolf, Greenfield & Sacks, P.C.

[57] ABSTRACT

An ambulatory physiological monitor includes a high capacity, plug connectable magnetic disk cartridge for storing physiological data and analysis software. The disk cartridge is easily removable from the monitor and is connectable to a remote computer for analysis of the physiological data using the analysis software stored in the disk cartridge. The ambulatory physiological monitor may include a wireless data modem for communicating with a remote computer system as to the patient's condition through a cellular telephone system. Selected portions of the physiological data or results of analysis of the physiological data may be transmitted to the remote computer system. The monitor may operate in a server mode in which it is controlled by the remote computer system. Updates to the analysis software and remote commands may be sent from the remote computer system to the monitor.

33 Claims, 11 Drawing Sheets

AMBULATORY PHYSIOLOGICAL MONITOR WITH REMOVABLE DISK CARTRIDGE AND WIRELESS MODEM

FIELD OF THE INVENTION

This invention relates to patient monitoring systems and, more particularly, to ambulatory physiological monitoring methods and apparatus.

BACKGROUND OF THE INVENTION

Monitoring of electrocardiography (ECG) data is a useful tool in diagnosing the condition of a patient's heart. A prominent type of ECG monitoring is Holter monitoring, in which ECG data is acquired continuously over a 24 hour period. Data acquired by Holter monitoring is useful in identifying patients who are at risk of ventricular tachycardia.

Ambulatory ECG monitors include several electrodes, which are attached to the patient, and a miniature recording unit. ECG signals acquired from the electrodes are stored by the recording unit for analysis. Typically, the recording unit is attached to a belt worn by the patient. The ambulatory monitor may be worn by the patient outside the hospital during the patient's normal daily routine.

Prior art ambulatory ECG monitoring systems have utilized several approaches for storing the ECG data. Tape-based systems are provided with a magnetic tape recorder that records ECG signals acquired from the electrodes. Tape-based systems have various drawbacks, including a limited frequency response, tape motion error problems and difficulty in encoding the occurrence of important events with precision. Solid state ambulatory ECG monitors utilize a memory, such as a random access memory (RAM), built into the recording unit. Presently available solid state systems must rely on data compression to store all the data generated during a recording session. The data compression involves a high degree of information loss. In addition, data held in the memory may be lost upon an interruption of power. An ambulatory medical monitor having a removable RAM package is disclosed in U.S. Pat. No. 4,592,018 issued May 27, 1986 to Wiegman.

An ambulatory physiological monitor containing a high capacity, miniaturized magnetic disk storage unit is disclosed in U.S. Pat. No. 5,228,450 issued Jul. 20, 1993 to Sellers. The disclosed ambulatory physiological monitor overcomes the problems associated with tape-based and solid state monitors and provides highly satisfactory performance. However, the disclosed monitor, as well as all other known prior art ambulatory physiological monitors, requires that the monitor be taken to a location having a specially adapted computer for analysis of the recorded data. The computer is specialized in the sense that it must have an adaptor for connection to the ambulatory physiological monitor to access the data stored therein and must be loaded with appropriate analysis software. In many instances, this process is inconvenient to the patient. An ambulatory ECG monitoring system wherein analysis software is stored within the ambulatory monitor is disclosed in U.S. Pat. No. 5,205,295 issued Apr. 27, 1993 to Del Mar et al.

Telemetry systems have also been utilized for transmitting ECG data from a patient to a monitoring location, typically in a hospital. An electrocardiographic telemetry and telephone transmission link system is disclosed in U.S. Pat. No. 3,882,277 issued May 6, 1975 to DePedro et al. A telemetry system which provides medical and location information to a host computer including a communication network is disclosed in U.S. Pat. No. 5,416,695 issued May 16, 1995 to Stutman et al. Another telemetry system which provides medical and location information is disclosed in U.S. Pat. No. 5,458,123 issued Oct. 17, 1995 to Unger. Additional telemetry systems for transmitting physiological data are disclosed in U.S. Pat. Nos. 5,153,584 issued Oct. 6, 1992 to Engira; 5,226,431 issued Jul. 13, 1993 to Bible et al; 5,417,222 issued May 23, 1995 to Dempsy et al; 5,113,869 issued May 19, 1992 to Nappholz et al; and 5,381,798 issued Jan. 17, 1995 to Burrows.

All of the known telemetry systems have had one or more disadvantages. Telemetry systems are typically designed for use within a limited geographical area, such as a hospital or the home. Thus, the patient's mobility is limited, and data is lost if the patient goes outside the coverage area of the system. In addition, such systems transmit raw data continuously, thus requiring a dedicated transmission channel. Finally, such systems are relatively complex and expensive.

SUMMARY OF THE INVENTION

According to a first aspect of the invention, a method for recording and analyzing physiological data from a patient is provided. The method comprises the steps of attaching an ambulatory physiological monitor containing a high capacity, miniaturized magnetic disk cartridge to an ambulatory patient, acquiring physiological data from the patient while the patient is ambulatory using the ambulatory physiological monitor, storing the physiological data acquired from the patient in the disk cartridge while the patient is ambulatory, removing the disk cartridge from the ambulatory physiological monitor and attaching the disk cartridge to a computer, and analyzing the physiological data stored in the disk cartridge with the computer. The disk cartridge preferably plugs into standard connectors in the ambulatory physiological monitor and in the computer.

According to a further feature of the invention, analysis software may be stored in the disk cartridge. When the disk cartridge is attached to the computer, at least a portion of the analysis software is transferred from the disk cartridge to the computer, and the physiological data is analyzed with the analysis software transferred from the disk cartridge to the computer.

According to another aspect of the invention, an ambulatory physiological monitor for recording physiological data from a patient for subsequent medical diagnosis of the patient is provided. The ambulatory physiological monitor comprises a housing, a high capacity, miniaturized magnetic disk cartridge located in the housing for storing physiological data and analysis software, and a circuit located in the housing for receiving a physiological signal representative of a physiological parameter of an ambulatory patient from a transducer attached to the ambulatory patient, for converting the physiological signal to the physiological data and for transferring the physiological data to the disk cartridge. The disk cartridge is plug connectable to the monitor and is easily removable from the monitor. The disk cartridge containing the physiological data and analysis software is plug is connectable to a remote computer for analysis of the physiological data using the analysis software in the disk cartridge.

According to a further aspect of the invention, a method for recording and analyzing physiological data from a patient is provided. The method comprises the steps of attaching an ambulatory physiological monitor containing a wireless data modem and a storage device to an ambulatory patient, the storage device having analysis software stored therein, acquiring physiological data representative of the patient's condition while the patient is ambulatory using the ambulatory physiological monitor, storing the physiological data acquired from the patient in the storage device while the patient is ambulatory, and communicating with a remote computer system as to the patient's condition through a cellular telephone system using the wireless data modem.

According to one feature of the invention, the physiological data stored in the storage device is analyzed using the analysis software to provide physiological information. The physiological information may be transmitted to the remote computer system in response to a request from the remote computer system, in response to a predetermined event in the physiological data or at predetermined intervals.

According to a further feature of the invention, new analysis software may be downloaded from the remote computer system to the ambulatory physiological monitor through the cellular telephone system using the wireless data modem. The new analysis software may be used to replace, modify or supplement the analysis software in the storage device.

According to a further feature of the invention, a portion of the physiological data may be selected based on a predetermined criteria in the analysis software. The selected physiological data may be transmitted to the remote computer system through the cellular telephone system using the wireless data modem.

According to still another feature of the invention, at least a portion of the analysis software may be transmitted to the remote computer system through the cellular telephone system using the wireless data modem. The analysis software may be used by the remote computer system for analyzing physiological data transmitted from the ambulatory physiological monitor.

According to still another aspect of the invention, an ambulatory physiological monitor for recording physiological data from a patient for a subsequent medical diagnosis of the patient is provided. The ambulatory physiological monitor comprises a housing, a storage device mounted in the housing for storing physiological data and analysis software, and a circuit mounted in the housing for receiving a physiological signal representative of a physiological parameter of an ambulatory patient from a transducer attached to the ambulatory patient, for converting the physiological signal to physiological data representative of the patient's condition and for transferring the physiological data to the storage device. The ambulatory physiological monitor further includes a wireless data modem mounted in the housing for communicating with a remote computer system as to the patient's condition through a cellular telephone system. The wireless data modem may comprise a cellular digital packet data modem. The storage device may comprise a high capacity, miniaturized magnetic disk cartridge.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
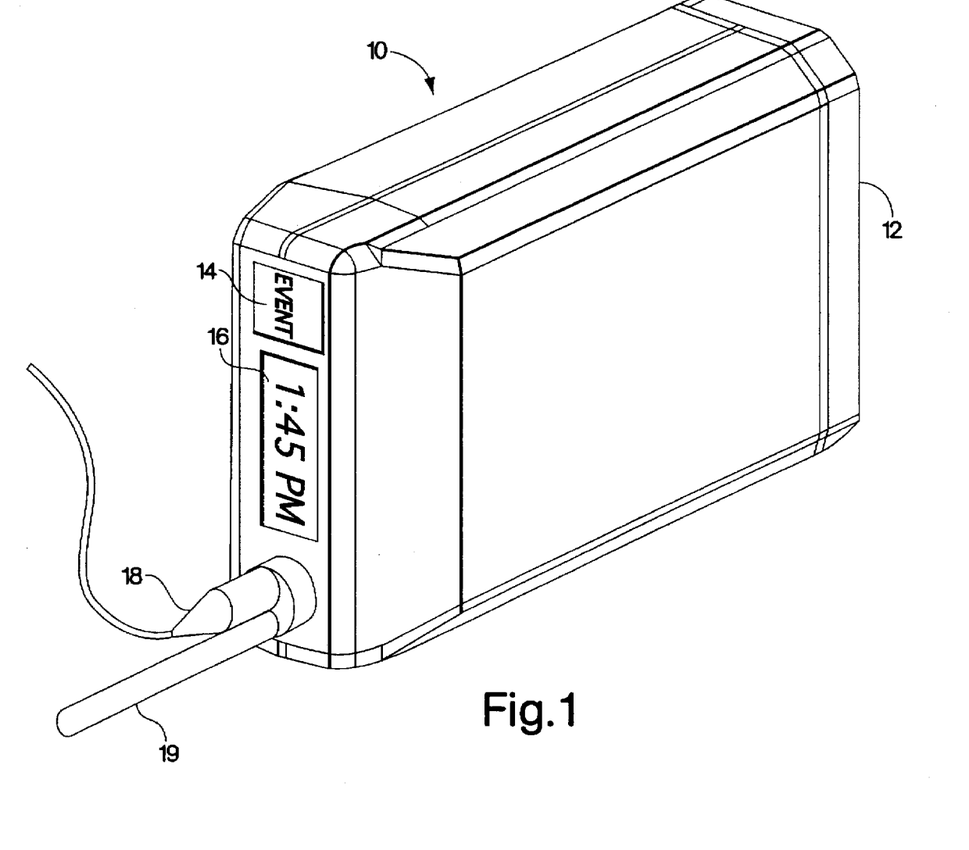
FIG. 1 is a perspective view of an ambulatory physiological monitor in accordance with the present invention.

A perspective view of an ambulatory physiological monitor 10 in accordance with the present invention is shown in FIG. 1. The elements of the monitor 10 are enclosed within a housing 12 which may be fabricated of a plastic material such as, for example, GE Noryl 2000. An event button 14, a user display 16, a patient connector 18 and an antenna 19 are located at one end of housing 12. The patient connector 18 provides an electrical connection between the circuitry of the ambulatory physiological monitor 10 and electrodes or other transducers affixed to the patient for monitoring the patient's condition. In a preferred embodiment, the ambulatory physiological monitor 10 has a generally rectangular shape with a length of about 5.1 inches, a width of about 3.2 inches and a thickness of about 1.5 inches. The monitor 10 may conveniently be worn on a patient's belt with a suitable attachment, such as a holster 11 shown in FIG. 3. In the preferred embodiment, the monitor 10 has a weight of about 14 ounces. The monitor 10 is carried by an ambulatory patient during the patient's normal activities, and the patient's physiological parameters of interest are recorded while the patient is ambulatory.

The user display 16 displays status messages and the time of day. The display 16 may be a conventional liquid crystal display (LCD). The event button 14 allows the patient to record the time of an event, such as the suffering of chest pains, so that the ECG data recorded at that time can be marked for closer examination. The antenna 19 is used for wireless communication as described below. In a preferred embodiment, the patient connector 18 and the antenna 19 are joined in a T-connector mounted in housing 12.

Figure 2A:
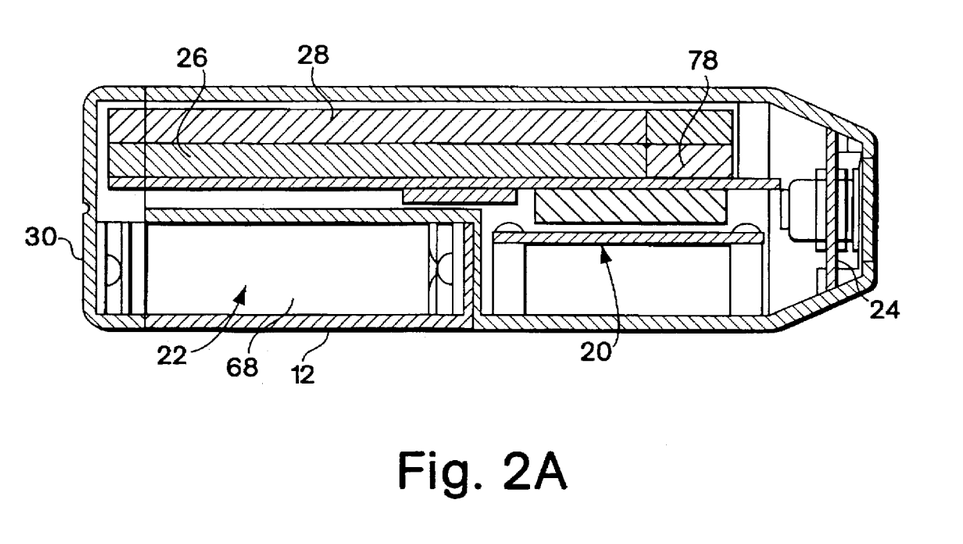
FIGS. 2A–2C are cross-sectional views of the ambulatory physiological monitor of FIG. 1.
Figure 2B:
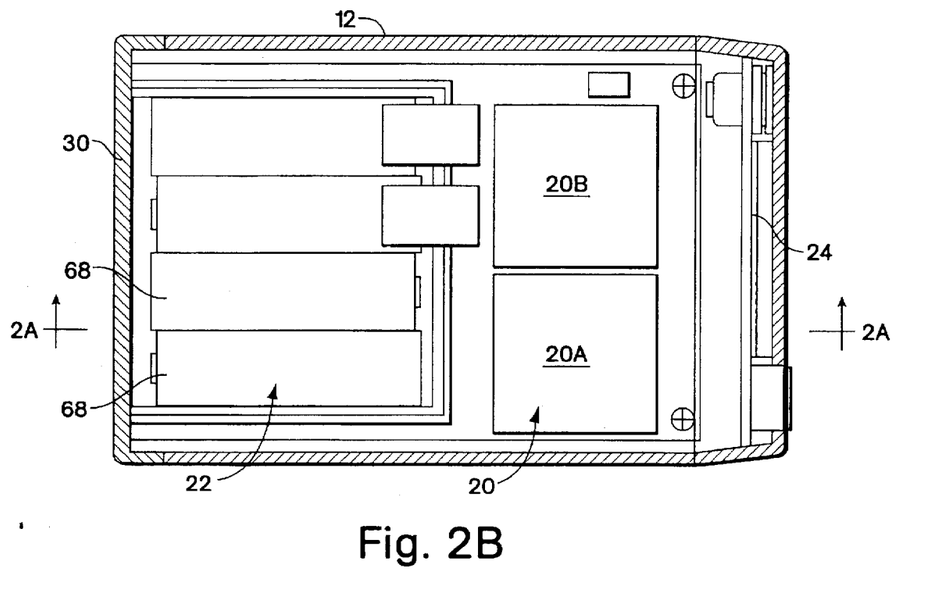
Figure 2C:
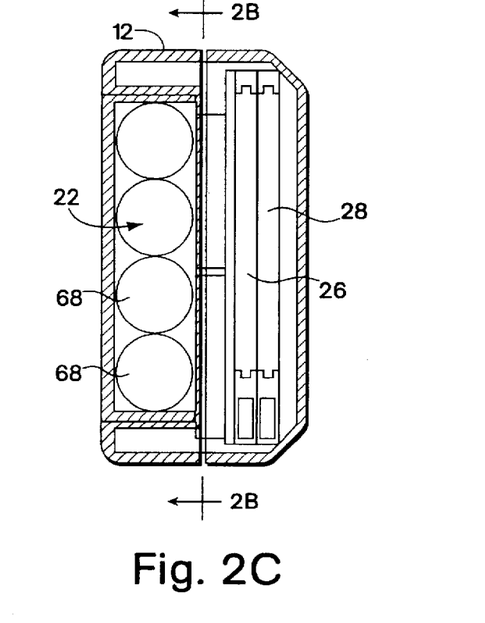

Cross sections of the ambulatory physiological monitor 10 are shown in FIGS. 2A–2C. The elements of the monitor 10 include an electronics module 20, a battery module 22, a display/user interface module 24 and a removable disk cartridge 26. The monitor 10 may optionally include a wireless data modem 28. The housing 12 includes a removable cover 30 which snaps onto the rear of monitor 10. The cover 30 is removed to provide access to battery module 22 and to permit removal or installation of disk cartridge 26. In the embodiment of FIGS. 2A–2C, the electronics module includes printed circuit boards 20A and 20B, and the display/user interface module 24 includes a printed circuit board for mounting of event button 14, user display 16, connector 18 and antenna 19. The elements of the monitor 10 are described in detail below.

Figure 3:
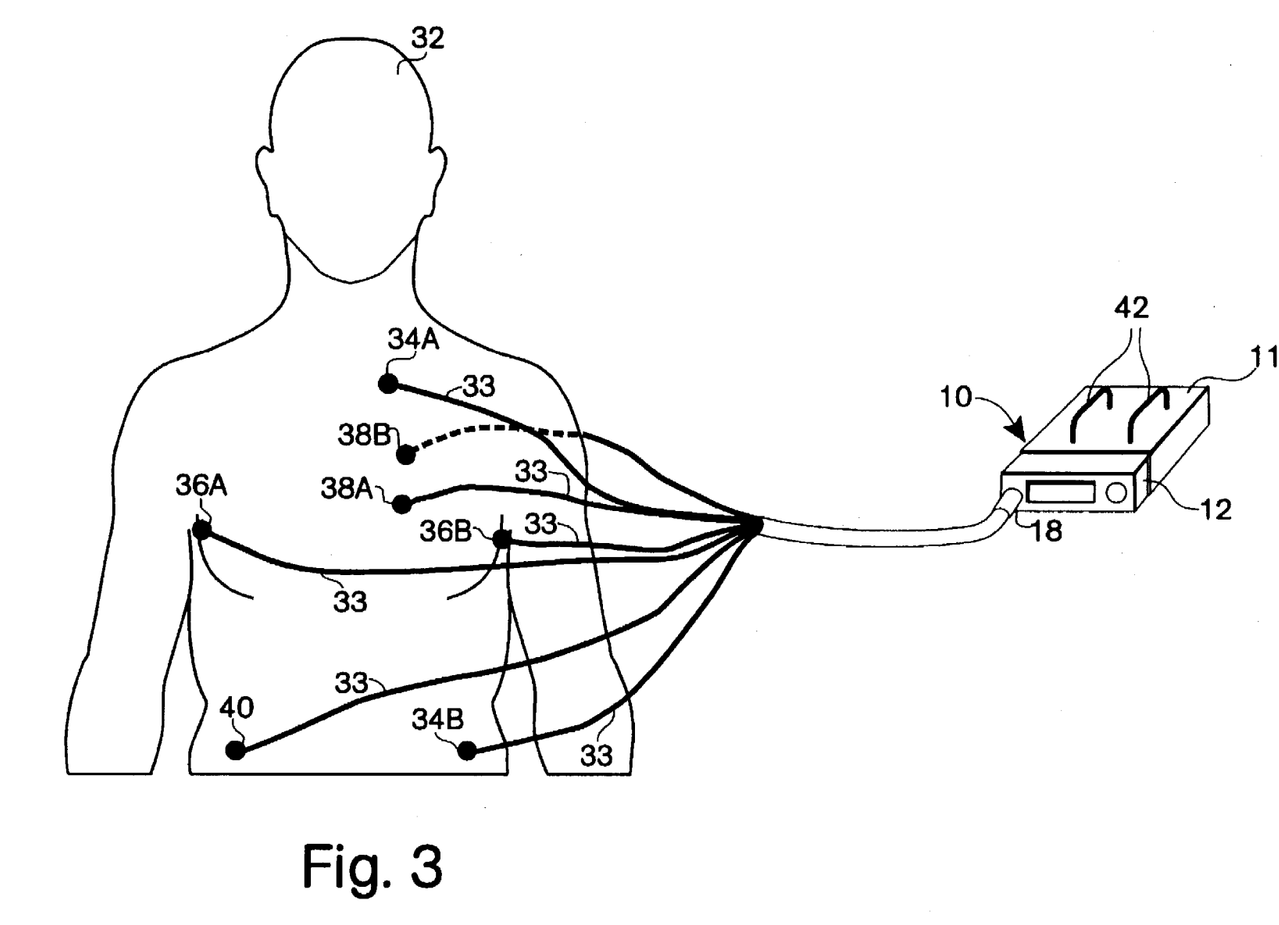
FIG. 3 is a pictorial view showing typical ECG electrode placements on a patient and the connection of the electrodes to the ambulatory physiological monitor.

The monitor 10 is used with a set of electrodes or other transducers. For most ECG applications, either two or three sets of electrodes are employed. As shown in FIG. 3, three sets of electrodes 34A, 34B, 36A, 36B, 38A and 38B are employed to provide a three-dimensional view of heart activity. The three pairs of electrodes provide ECG signals from X, Y and Z axes of the patient, respectively. Each electrode is connected to monitor 10 via a lead wire 33 and connector 18. The lead wire 33 for electrode 38B is shown in phantom in FIG. 3, because the electrode is placed on the patient's back. This pattern of electrode replacement corresponds to a standard established by the Association for the Advancement of Medical Instrumentation (AAMI). A ground electrode 40 is also utilized. The electrodes may be conventional ECG silver chloride electrodes. As indicated previously, the monitor 10 may be positioned in holster 11 for attachment to the patient's belt with belt loops 42. The monitor 10 may be worn or carried by the patient in any desired manner that does not interfere with recording of physiological data.

Figure 4:
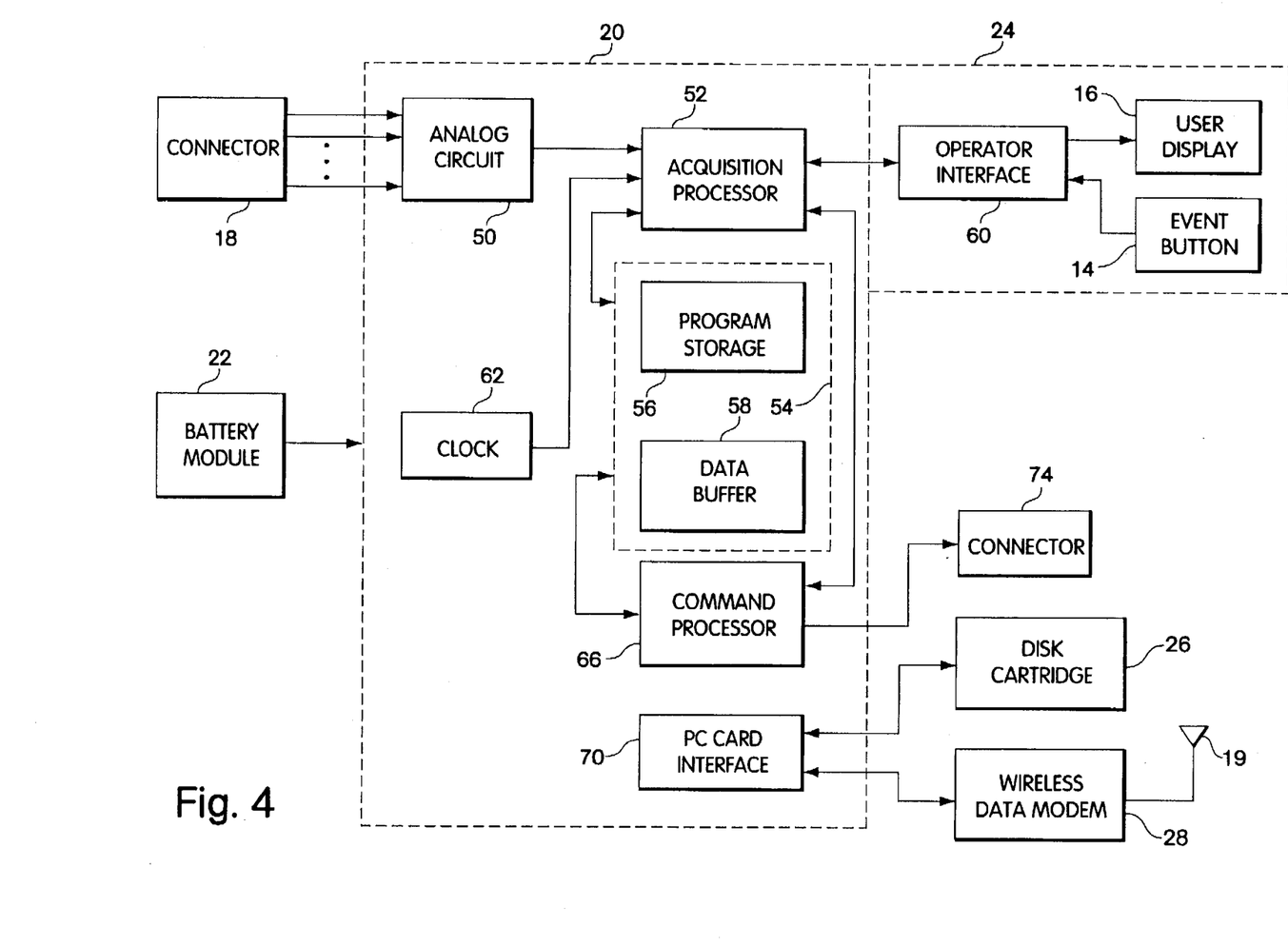
FIG. 4 is a block diagram of the components of the ambulatory physiological monitor.

A block diagram of the ambulatory physiological monitor 10 is shown in FIG. 4. The contacts in patient connector 18 are connected to an analog circuit 50 in electronics module 20. As indicated above, electrodes attached to the patient are electrically connected through connector 18 to the monitor 10. The analog circuit 50 amplifies and processes ECG signals from the patient electrodes. A suitable analog circuit is disclosed in U.S. Pat. No. 5,228,450, which is hereby incorporated by reference. The outputs of analog circuit 50 are connected to an acquisition processor 52, which controls a portion of the monitor operation and converts amplified analog ECG signals into digital data words. The acquisition processor 52 is connected to a memory 54 which includes a program storage area 56 and a data buffer 58. The program storage area 56 is used to store a program for controlling operation of the acquisition processor 52. Data buffer 58 provides temporary storage of ECG data. The acquisition processor 52 is connected through an operator interface 60 to event button 14 and user display 16. Acquisition processor 52 records the times when the event button 14 is activated by the patient. The user display 16 normally displays the time of day and can be used to provide other status messages to the patient. A real-time clock 62 is connected to acquisition processor 52.

A command processor 66 is connected to acquisition processor 52 and to memory 54. The command processor 66 is further connected through a PC Card interface 70 to disk cartridge 26 and to wireless data modem 28. The PC Card interface 70 includes I/O drivers and power supplies for the disk cartridge 26 and the wireless data modem 28. The program storage area 56 is used to store a program for controlling operation of the command processor 66. ECG data is transferred at intervals by the command processor 66 from data buffer 58 to disk cartridge 26. The command processor 66 also controls transmission and reception of information through wireless data modem 28 as described below. The command processor 66 is coupled to a connector 74 which permits serial communication with devices such as a printer or an instrument.

Each of the processors 52 and 66 is preferably implemented as a single chip microprocessor. A suitable microprocessor is the type 87C451, manufactured by Philips Semiconductor. This device includes an analog-to-digital converter which is used by the acquisition processor 52 for converting analog ECG signals to digital data words. The memory 54 is preferably implemented as flash memory having a capacity of 4 megabytes. The memory 54 has sufficient capacity to store programs for operation of the processors 52 and 66 and for temporary storage of ECG data. Suitable memory devices include the Samsung KM29N16000.

The battery module 22 provides electrical power to electronics module 20, disk cartridge 26, wireless data modem 28 and display/user interface module 24. As described below, portions of the monitor 10 are powered down when not in use to save battery power. In a preferred embodiment, the battery module 22 contains four AA alkaline batteries 68 (FIGS. 2A–2C), sufficient to power the ambulatory physiological monitor 10 for 24 hour operation.

Figure 5:
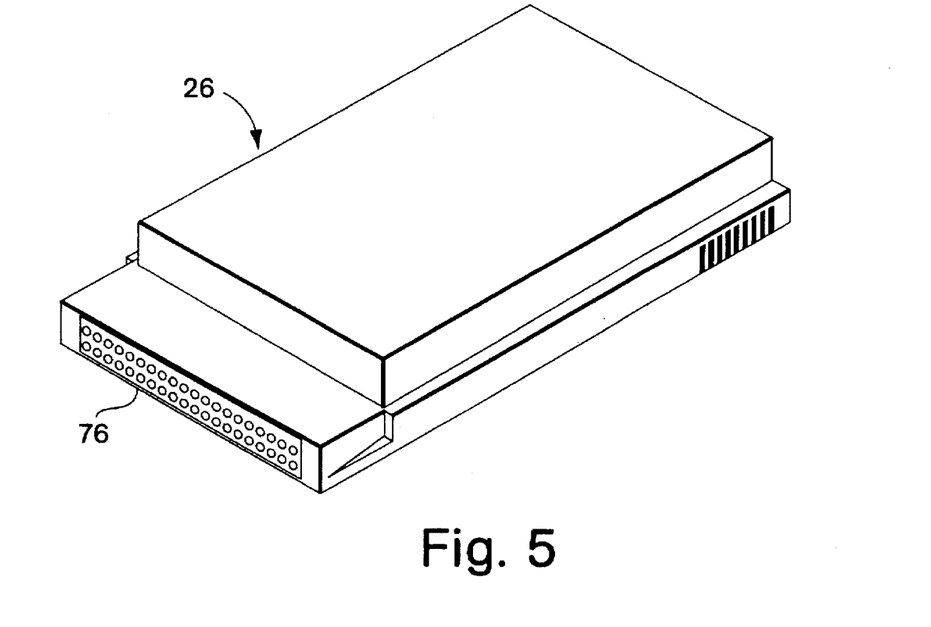
FIG. 5 is a perspective view of the removable disk cartridge used in the ambulatory physiological monitor of FIG. 1.

The disk cartridge 26 is preferably a high capacity, miniaturized disk cartridge that is plug connectable in the ambulatory physiological monitor 10. The disk cartridge may be one that meets the PC Card standard developed by the Personal Computer Memory Card Industry Association (PCMCIA). The PC Card standard may be used to implement various memory devices, including disk drives and flash memories. A perspective view of the PC Card configuration of disk cartridge 26 is shown in FIG. 5. The module has a generally rectangular configuration, with a connector 76 that mates with a fixed connector 78 (FIG. 2A) in the monitor 10. Thus, the disk cartridge 26 is easily removable from the monitor 10. PC Card modules have dimensions of 54 mm×85.6 mm (approximately the size of a credit card) and thicknesses of 3.3 mm (Type I), 5.0 mm (Type II) or 10.5 mm (Type III). Disk cartridges with capacities up to 500 megabytes are available in accordance with the PC Card standard. In a preferred embodiment, the monitor 10 utilizes a Type III disk cartridge having a capacity of 170 megabytes available from Integral Peripherals. Important features of the disk cartridge are that it be sufficiently small to fit in the monitor 10, that it have sufficient capacity to store 24 hours of uncompressed physiological data and that it be plug connectable to the monitor 10.

In an alternative embodiment, the disk cartridge 26 may be replaced with a PC Card module containing flash memory. Flash memory modules configured in accordance with the PC Card standard described above are available from SanDisk Corporation, as the SDP5 series. Presently available flash memory PC Card modules provide up to 40 megabytes of storage capacity. This capacity is not sufficient to record 24 hours of uncompressed ECG data. However, the flash memory PC Card module can be used in applications where less than 24 hour recording is acceptable. It is expected that the storage capacity of flash memory PC Card modules will increase in the near future.

The wireless data modem 28 is preferably one that meets the cellular digital packet data (CDPD) standard. The CDPD standard is an industry standard that allows the wireless transmission of data over the existing cellular networks. Designed to leverage the existing cellular technology infrastructure and equipment, CDPD technology utilizes the Internet protocol scheme, making it compatible with very large installed base of networks and applications. CDPD technology takes advantage of moments during usage of a cellular telephone channel when the channel is idle. CDPD technology detects and utilizes the idle moments by packaging data in small packets and sending it in short bursts during the idle time. CDPD radio transceivers are available, for example, from Cincinnati Microwave. Preferably, the wireless data modem is configured as a PC Card module as described above. In an alternative embodiment, the wireless data modem 28 may be permanently installed within the ambulatory physiological monitor 10. The wireless data modem 28 permits transmission and reception of data through the cellular telephone network as described below. The wireless data modem 28 may be omitted from monitor 10 when wireless communication is not required.

The data buffer 58 is used for temporary storage of ECG data. The data buffer 58 permits the command processor 66, PC Card interface 70 and disk cartridge 26 to be powered down during a major portion of the 24 hour Holter recording session, thus saving battery power. ECG signals from the patient electrodes are continuously sampled and converted to digital data words (ECG data) by acquisition processor 52. The ECG data is stored by acquisition processor 52 in data buffer 58. During this time, the command processor 66, PC Card interface 70 and disk cartridge 26 are powered down. When the acquisition processor 52 detects that the data buffer 58 is nearly full, the command processor 66, PC Card interface 70 and disk cartridge 26 are powered on. The command processor 66 then transfers the ECG data in the data buffer to the disk cartridge 26. This operation takes a relatively short time, typically about 20 seconds. Then, the command processor 66, PC Card interface 70 and disk cartridge 26 are again powered down, and the acquisition processor 52 continues storing ECG data in the data buffer 58. Typically, the transfer of data from data buffer 58 to disk cartridge 26 is repeated on the order of once every 80 minutes. As a result, the battery module 22 has sufficient capacity for operation over a 24 hour period. It will be understood that the acquisition and storage of ECG data in data buffer 58 proceeds without interruption during transfer of data from data buffer 58 to disk cartridge 26. Intermittent transfer of ECG data to a disk is described in further detail in U.S. Pat. No. 5,228,450.

Figure 6:
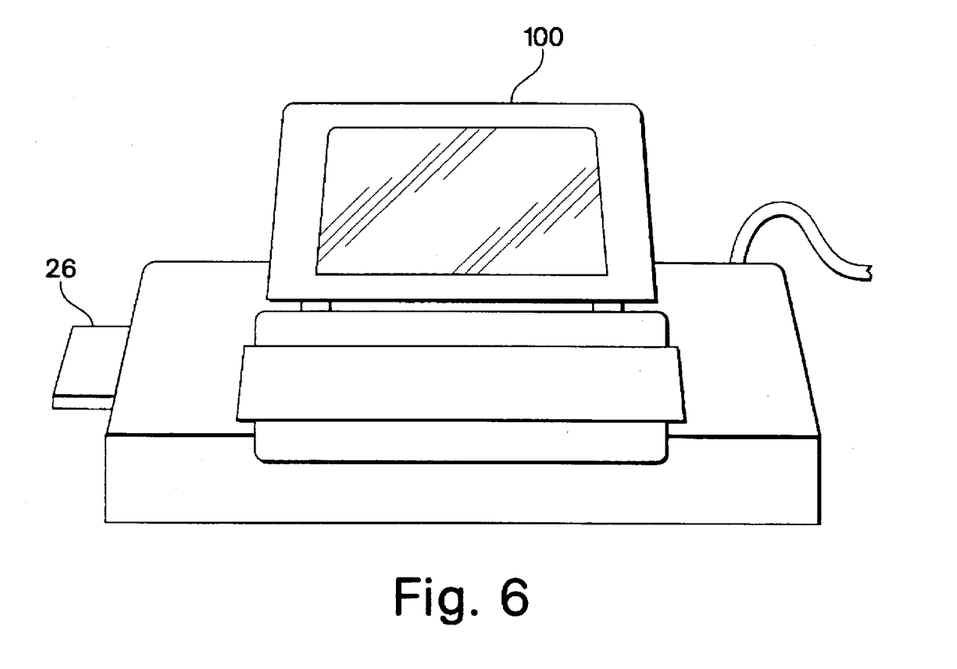
FIG. 6 illustrates connection of the disk cartridge to a computer system.

As indicated above, the disk cartridge 26 is removable from the ambulatory physiological monitor 10. After recording of the ECG data or other physiological data has been completed, typically over a period of 24 hours, the disk cartridge 26 is removed from the monitor 10 by removing connector 76 from its mating connector 78 in monitor 10. Preferably, the disk cartridge 26 also stores an analysis program for analysis of the ECG data. Techniques for analysis of ECG data are well known to those skilled in the art. The disk cartridge containing ECG data and the analysis program is taken to a suitable computer 100 as shown in FIG. 6. The computer 100 may be any computer having a PC Card slot, including a connector for receiving a PC Card module and circuitry for interfacing with the PC Card module. The computer 100 is typically a conventional personal computer (PC). The computer 100 is not required to have pre-installed software for accessing and analyzing the ECG data. The disk cartridge 26 is plugged into the PC Card slot in the computer 100. In accordance with conventional protocols for interfacing with PC Card modules, the computer 100 reads the information on the disk cartridge 26 and loads relevant portions of the analysis program into its memory. The computer 100 then executes the analysis program and analyzes the ECG data contained on the disk cartridge 26.

As indicated above, the computer 100 may be any computer that is equipped with a connector and circuitry for operation with a PC Card module that meets the PC Card standard described above. Since PC Card modules are becoming relatively common, PC's having PC Card slots are also becoming common. Thus, the computer 100 is not required to have a connector which is specially adapted for connection to the ambulatory physiological monitor 10. Furthermore, the computer 10 is not required to have pre-installed ECG analysis software. Thus, the ECG data contained on disk cartridge 26 can be analyzed on any PC having a PC Card slot, for example in a doctor's office, and the patient is not required to travel to a location having specialized equipment for analysis of the ECG data.

Figure 7:
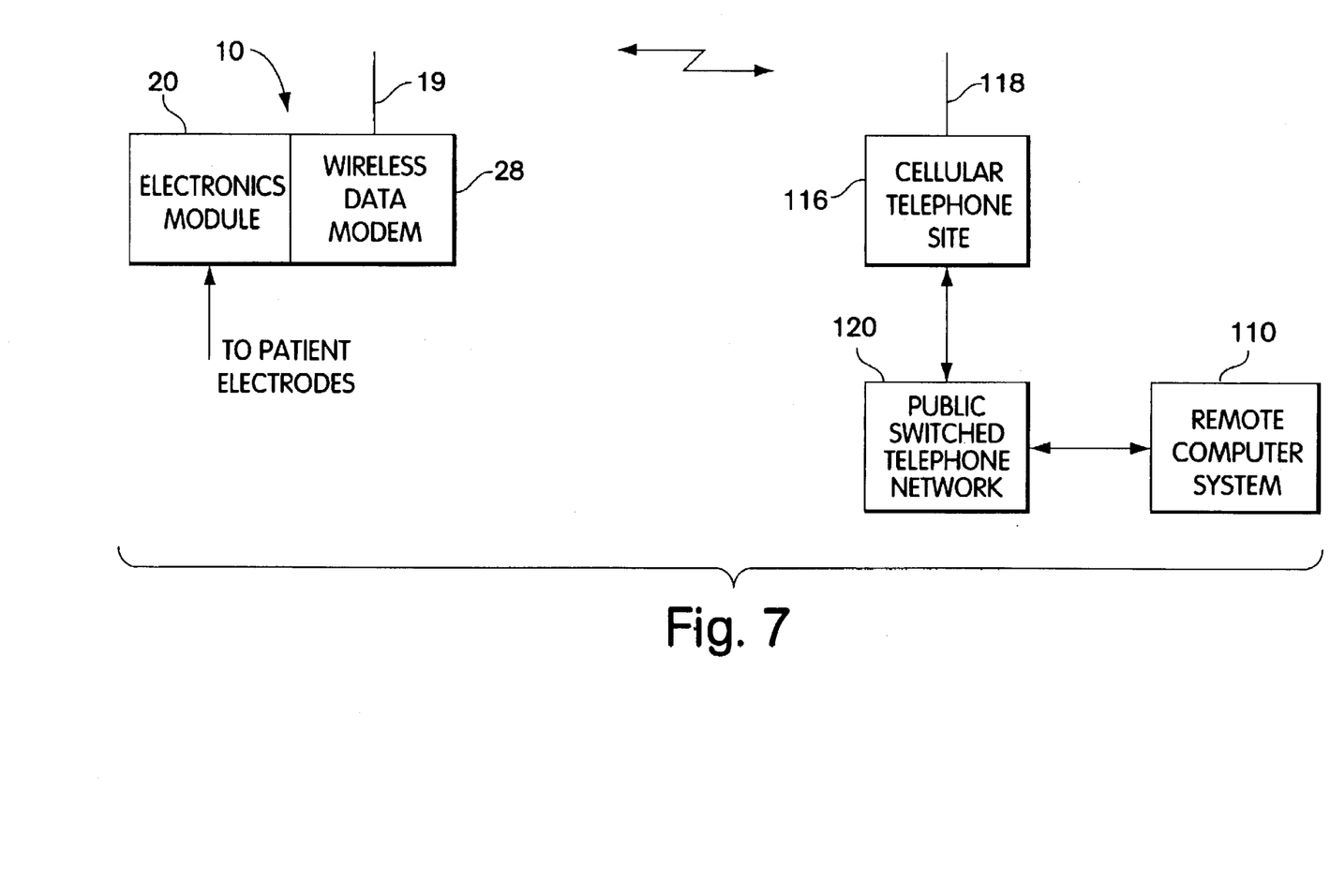
FIG. 7 is a block diagram of the elements associated with wireless communication between the ambulatory physiological monitor and a remote computer system.

A block diagram illustrating use of the wireless data modem 28 is shown in FIG. 7. The wireless data modem 28 permits the ambulatory physiological monitor 10 to transmit information to a remote computer system 110 and to receive information from the remote computer system 110 via a radio link 112. The wireless data modem 28, having antenna 19, preferably communicates through a cellular telephone site 116, having an antenna 118. The cellular site 116 is one that is equipped for communication in accordance with the cellular digital packet data standard. The cellular telephone site 116 communicates with remote computer 110 through the public switched telephone network 120. Communication through the telephone network 120 may utilize a dial-up line or may utilize the Internet. The communication system illustrated in FIG. 7 differs from conventional telemetry systems, because information is transmitted and received in packets, typically during relatively short time periods. By contrast, telemetry systems typically transmit data continuously and thus require a dedicated communication channel. The system of FIG. 7 has the advantage that communication can occur whenever the patient carrying the monitor 10 is within range of a cellular telephone site that has CDPD capability. As cellular sites with CDPD capability become more widespread, this restriction will not be significant. Thus, the patient is not limited as to location during a monitoring session.

Communication between the ambulatory physiological monitor 10 and the remote computer system 110 through the wireless modem 28 can be implemented in a variety of different ways. The following are examples of operations that can be performed.

1. Selected portions of the ECG data can be transmitted from the monitor 10 to the remote computer system 110. Selection of data can be based on a variety of criteria. For example, a block of ECG data before and after activation of the event button by the patient can be transmitted to the remote computer system 110. In another approach, the selection of ECG data for transmission can be automatic. Thus, when a predefined event occurs in the ECG data, a block of ECG data associated with that event is transmitted to the remote computer system. In yet another approach, a block of ECG data can be transmitted at predefined intervals, such as once per hour. In still another approach, the remote computer system 110 can transmit a message to the monitor 10 through the wireless data modem 28 requesting a selected block of ECG data. In response, the selected block of ECG data is transmitted to the remote computer system 110.

2. The command processor 66 in the monitor 10 can analyze all or a portion of the ECG data stored on disk cartridge 26 to provide ECG information representative of the condition of the patient. The ECG information which results from the analysis operation is transmitted to the remote computer system 110 through wireless data modem 28. Initiation of analysis by the command processor 66 can be automatic or by command from the computer system 110. The remote computer system can request that different algorithms of the analysis program be executed. Execution of the analysis program can also be initiated by activation of the event button, by a predefined event in the ECG data or at predefined intervals.

3. The operating mode of the ambulatory physiological monitor 10 can be changed by command from the remote computer system 110 through wireless data modem 28. For example, the monitor 10 can be changed from normal to high resolution mode by remote command.

4. The remote computer system 110 can download modifications and additions to the software in the monitor 10.

Thus, for example, an analysis algorithm may be altered, or a new analysis algorithm may be downloaded to the monitor 10 through wireless data modem 28.

5. Analysis routines can be transmitted from the monitor 10 to the remote computer system 110 to enable analysis of the ECG data by the remote computer system.

6. The monitor 10 can operate in a server mode in which it is controlled by the remote computer system 110. In the server mode, the remote computer system 110 has access to the files of monitor 10 and effectively functions as a terminal for controlling monitor 10.

Figure 8:
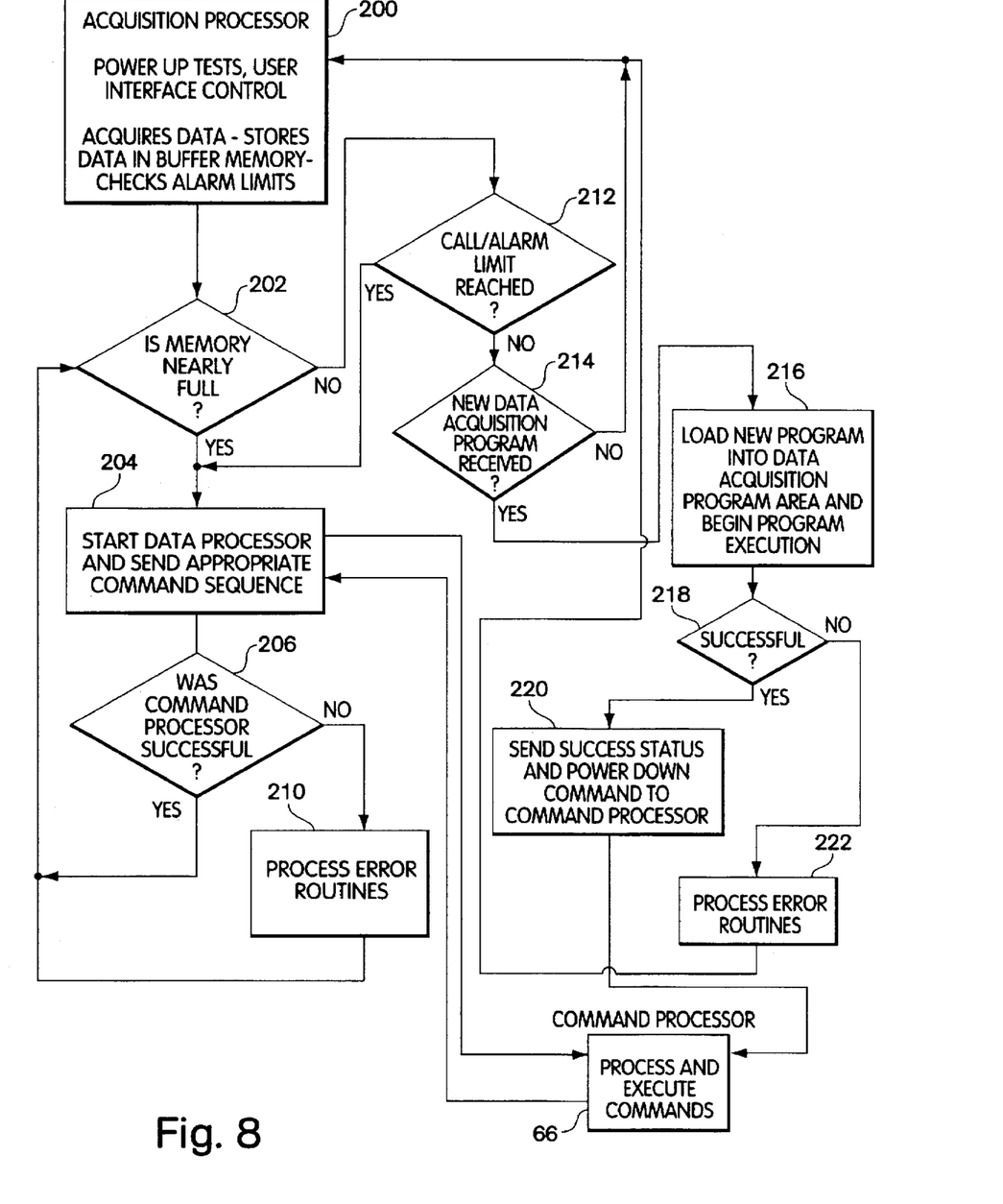
FIG. 8 is a flow diagram of the operations performed by the acquisition processor of FIG. 3.

A flow chart of the operations performed by the acquisition processor 52 is shown in FIG. 8. As shown in step 200, the acquisition processor 52 performs power up tests of the monitor 10 and controls the user interface, including event button 14 and user display 16. In addition, the acquisition processor 52 acquires ECG signals from analog circuit 50, converts the signals to ECG data and stores the data in data buffer 58. These operations are described in more detail in U.S. Pat. No. 5,228,450. The acquisition processor 52 also checks alarm limits with respect to the ECG data. For example, the acquisition processor 52 may check the ECG data for the occurrence of abnormal heartbeats. In step 202, the acquisition processor 52 determines whether the data buffer 58 is nearly full. When the data buffer is nearly full, the acquisition processor 52 starts the command processor 66 in step 204. The acquisition processor 52 causes the command processor 66 and the disk cartridge 26 to be powered up. Then a command to transfer ECG data from the data buffer 58 to the disk cartridge 26 is sent to the command processor 66. Upon completion of the data transfer, the command processor 66 notifies the acquisition processor 52 via a status message if the transfer operation was successful. If the acquisition processor determines in step 206 that the command processor operation was successful, the acquisition processor 52 returns to step 202. When the command processor did not successfully transfer ECG data from the data buffer 58 to disk cartridge 26, error routines are processed by the acquisition processor 52 in step 210. The acquisition processor then returns to step 202.

When the data buffer 58 is not nearly full, as determined in step 202, the acquisition processor determines in step 212 whether a call/alarm limit has been reached. When a call/alarm limit has been reached, the acquisition processor 52 starts the command processor 66 in step 204 and sends a command requesting the command processor to execute a call/alarm limit routine. This may involve storing the parameters of the call/alarm limit on the disk cartridge 26 and/or transmitting a message via the wireless data modem 28. When the call/alarm limit has not been reached, the acquisition processor 52 determines in step 214 whether a new data acquisition program has been received. If a new data acquisition program has been received, the new program is loaded into the program storage area 56 and program execution is initiated in step 216. If loading and execution of the new program is determined to be successful in step 218, the acquisition processor 52 sends a success status message and a power down command to the command processor 66 in step 220. If the new program is not successfully loaded, the acquisition processor 52 processes error routines in step 222 and returns to step 200 to continue data acquisition in accordance with the existing data acquisition program. When a new data acquisition program has not been received, the acquisition processor 52 returns to step 200 and continues with data acquisition in accordance with the existing data acquisition program.

Figure 9:
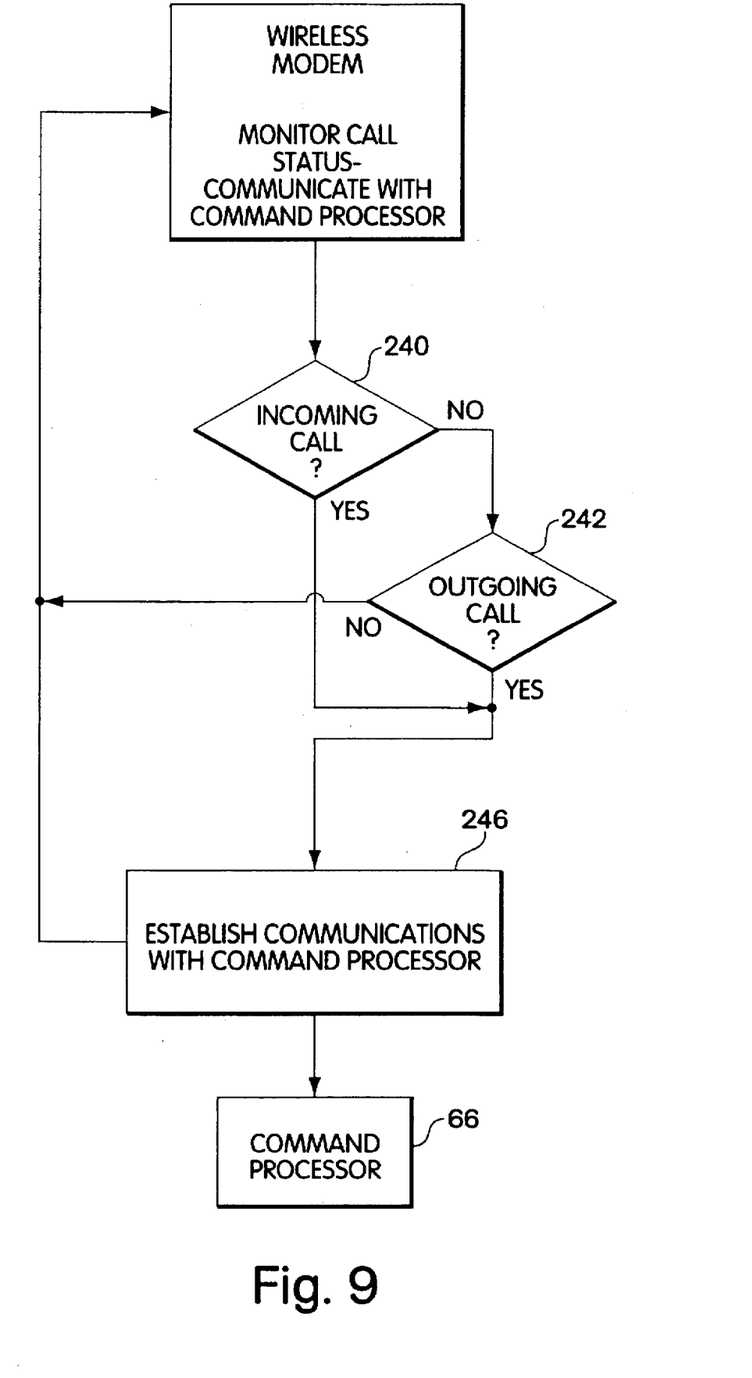
FIG. 9 is a flow diagram of the operations performed by the wireless data modem of FIG. 3.

A flow diagram of the operations performed by the wireless data modem 28 is shown in FIG. 9. The wireless data modem looks for an incoming call from the remote computer system 110 in step 240 and looks for an outgoing call from the command processor 66 in step 242. When an incoming call is received, the wireless data modem 28 establishes communication with the command processor 66 in step 246 and forwards the incoming data to the command processor 66. When the wireless data modem 28 identifies an outgoing call, communication with the command processor 66 is established in step 246. The wireless data modem transmits data received from the command processor to the remote computer system 110 as described above. When an incoming call or an outgoing call is not in process, the wireless data modem is an idle state in which it can identify incoming and outgoing calls but is otherwise powered down.

Figure 10A:
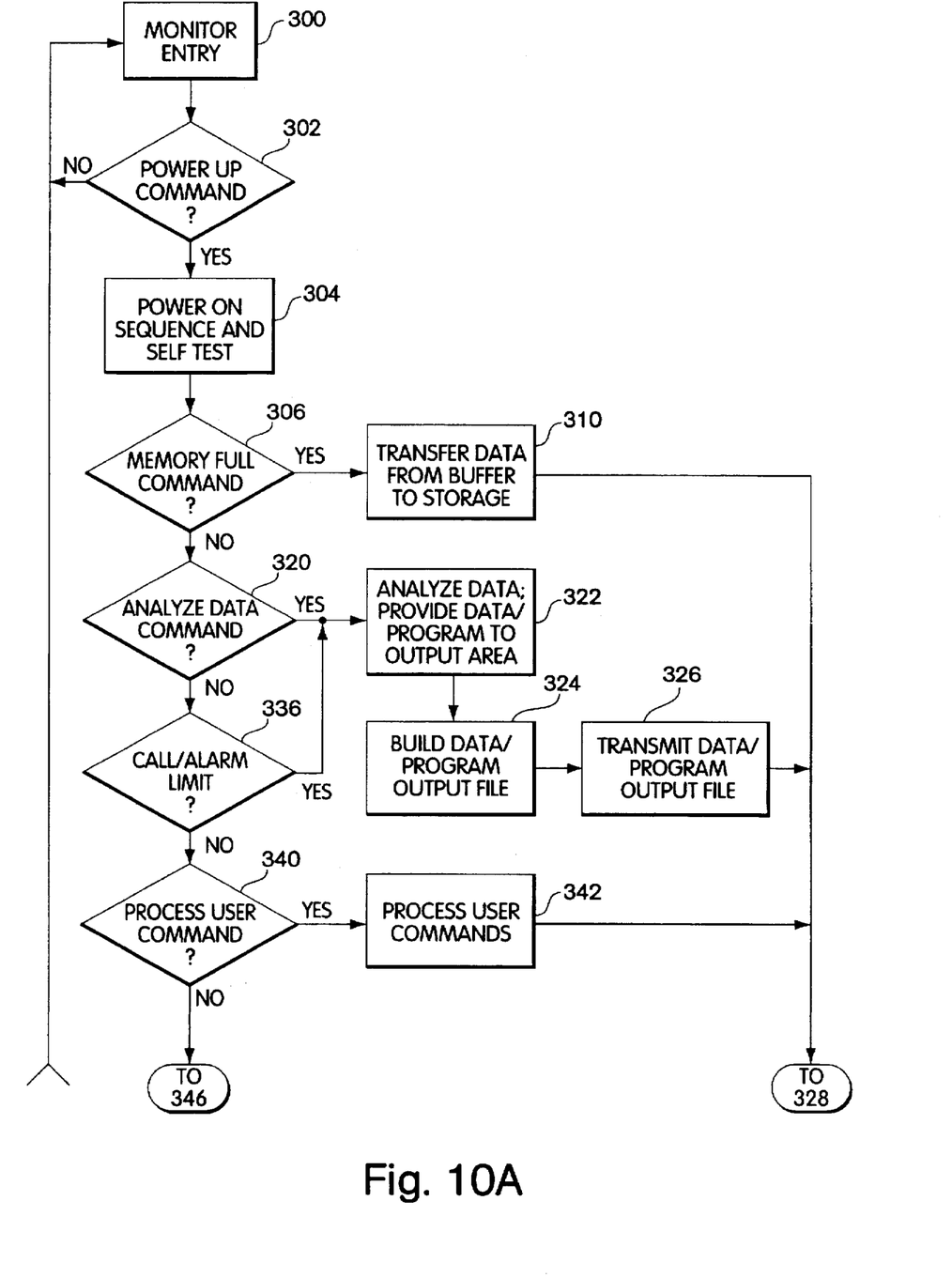
FIGS. 10A and 10B are a flow diagram of the operations performed by the command processor of FIG. 3.
Figure 10B:
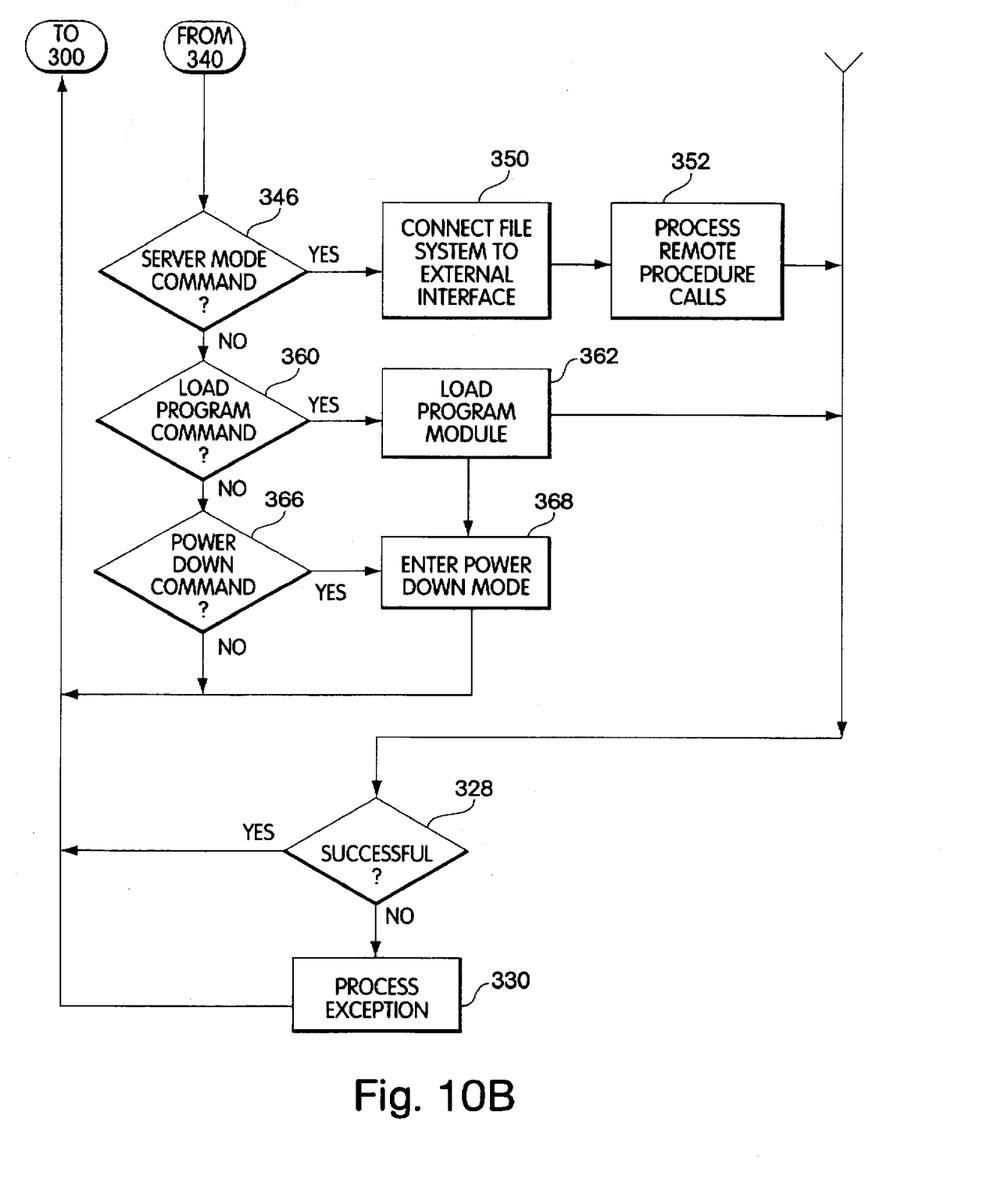

A flow diagram of the operations performed by the command processor 66 is shown in FIGS. 10A–10B. The command processor is normally powered down and waiting for commands from the acquisition processor 52 or the wireless data modem 28 in step 300. In the idle state, the command processor 66 is partially powered on so that it may receive commands from the acquisition processor 52 and the wireless data modem 28. When a power up command is received in step 302, the command processor 66 performs a power on sequence and self test in step 304.

When a memory full command is identified in step 306, the command processor transfers ECG data from data buffer 58 to disk cartridge 26 in step 310. If the data transfer is determined in step 328 to be successful, command processor returns to step 300 and notifies the acquisition processor 52 via a status message that the transfer was successfully completed. If the data transfer was not successful, the command processor executes an error routine in step 330 and returns to step 300. The acquisition processor 52 is notified by the command processor 66 that the data transfer was not successful.

If an analyze data command is identified in step 320, the requested analysis is performed by the command processor 66 in step 322, and the results are transferred into a data output area. Output files are built in step 324. In step 326, the output file is transmitted via the wireless data modem 28 or is written to the disk cartridge 26. The destination of the output file depends on the particular command received. When the analyze data command is successfully executed, as determined in step 328, the command processor 66 returns to step 300 and sends a success status message to the acquisition processor 52 or the wireless data modem 28. When the analyze data command is not successfully executed, an error routine is executed in step 330, and the command processor returns to step 300. The acquisition processor or the wireless modem is notified that the analyze data command was not successfully executed.

If the command processor 66 identifies a call/alarm limit command in step 336, any necessary analysis is performed by the command processor in step 322. The output file is built in step 324, and information regarding the call/alarm limit is transmitted via the wireless data modem 28 or is written to the disk cartridge 26 in step 326.

If the command processor 66 identifies a command to process user installed command in step 340, the user installed commands are processed in step 342. User installed commands are commands to the monitor 10 by the remote computer system 110. Examples of user installed commands include commands to perform heart rate variability analysis and analysis of ECG late potentials. After the user installed commands are processed, the command processor proceeds to step 328.

If a server mode command is identified in step 346, the file system in the monitor 10 is connected to the external interface in step 350. In the server mode, the remote computer system 110 is in control of the ambulatory physiological monitor 10. In this mode, the remote computer system 110 can, for example, access ECG data and other files in the monitor 10, modify the analysis program, alter alarm limits and the like. The command processor processes remote procedure calls from the remote computer system 110 in step 352 and proceeds to step 328.

If a load program command is identified in step 360, the program is loaded from disk cartridge 26 to memory 54 in step 362. The load program command may, for example, be used to load a new or modified program that was transferred from the remote computer system 110 to disk cartridge 26 in the server mode. The command processor 66 proceeds from step 362 to step 328.

If a power down command is identified in step 366, the power down mode is entered in step 368. The command processor then returns to step 300 to wait for additional commands.

The ambulatory physiological monitor 10 has been described in connection with ECG monitoring using ECG electrodes attached to the patient. It will be understood that the ambulatory physiological monitor of the present invention can be used for monitoring other physiological parameters of the patient. Examples of such parameters include respiration, EEG, blood pressure, blood oxygen content and respiration $CO_2$ content. Different types and numbers of transducers may be utilized in connection with monitoring the condition of the patient. In general, the monitor of the present invention acquires, processes and stores data representative of one or more physiological parameters of the patient. The physiological parameters may be ECG signals or other physiological parameters.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for recording and analyzing physiological data from a patient, comprising the steps of:
    attaching an ambulatory physiological monitor containing a high capacity, miniaturized magnetic disk cartridge to an ambulatory patient;
    acquiring physiological data from the patient while the patient is ambulatory using said ambulatory physiological monitor;
    storing the physiological data acquired from the patient in said disk cartridge while the patient is ambulatory;
    storing analysis software in said disk cartridge;
    removing said disk cartridge from said ambulatory physiological monitor and attaching said disk cartridge to a computer;
    transferring at least a portion of said analysis software from said disk cartridge to said computer when said disk cartridge is attached to said computer; and
    analyzing the physiological data stored in said disk cartridge with said computer, wherein the step of analyzing the physiological data is performed with the analysis software transferred from said disk cartridge to said computer.

2. A method as defined in claim 1 further including the steps of identifying an alarm condition when the physiological data meets an alarm criteria and storing information representative of the alarm condition in said disk cartridge.

3. A method as defined in claim 1 wherein the step of acquiring physiological data includes the steps of converting a physiological signal to physiological data and storing the physiological data in a data buffer, and wherein the step of storing the physiological data includes transferring the physiological data from the data buffer to said disk cartridge.

4. A method as defined in claim 1 further including the steps of storing analysis software in said disk cartridge and analyzing at least a portion of the physiological data stored in said disk cartridge in said ambulatory physiological monitor.

5. An ambulatory physiological monitor for recording physiological data from a patient for subsequent medical diagnosis of the patient, comprising:
    a housing;
    a high capacity, miniaturized magnetic disk cartridge mounted in said housing for storing physiological data and analysis software; and
    a circuit, located in said housing, for receiving a physiological signal representative of a physiological parameter of an ambulatory patient from a transducer attached to the ambulatory patient, for converting said physiological signal to said physiological data and for transferring said physiological data to said disk cartridge;
    wherein said disk cartridge is plug connectable in said monitor and is easily removable from said monitor, said disk cartridge being connectable to a remote computer for transfer of said physiological data and at least a portion of said analysis software from said disk cartridge to the remote computer for analysis of said physiological data using the analysis software stored in said disk cartridge and transferred, at least in part, to the remote computer.

6. An ambulatory physiological monitor as defined in claim 5 wherein said circuit includes a data buffer, an acquisition processor for converting said physiological signal to said physiological data and for storing said physiological data in said data buffer, and a command processor for transferring said physiological data from said data buffer to said disk cartridge when said data buffer is nearly full.

7. An ambulatory physiological monitor as defined in claim 5 wherein said disk cartridge comprises a PC Card module.

8. An ambulatory physiological monitor as defined in claim 5 further including a wireless data modem for wireless communication with a remote computer system.

9. A method for recording and analyzing physiological data from a patient, comprising the steps of:
    attaching an ambulatory physiological monitor containing a wireless data modem and a storage device to an ambulatory patient, said storage device having analysis software stored therein;
    acquiring physiological data from the patient while the patient is ambulatory using said ambulatory physiological monitor;
    storing the physiological data acquired from the patient in said storage device while the patient is ambulatory, said physiological data representing the patient's condition; and
    communicating with a remote computer system as to the patient's condition through a cellular telephone system using said wireless data modem, the step of communicating with said remote computer system being performed using a cellular digital packet data modem for transmitting and receiving data packets.

10. A method as defined in claim 9 further including the step of analyzing the physiological data stored in the storage device, using said analysis software, to provide physiological information and wherein the step of communicating with said remote computer system includes transmitting said physiological information to said remote computer system.

11. A method as defined in claim 10 wherein the step of transmitting said physiological information to said remote computer system is executed in response to a predetermined event in said physiological data.

12. A method as defined in claim 10 wherein the step of communicating with said remote computer system includes downloading new analysis software from said remote computer system to said ambulatory physiological monitor through said cellular telephone system using said wireless data modem, said new analysis software being used to replace, modify or supplement the analysis software in said storage device.

13. A method as defined in claim 9 further including the step of selecting a portion of said physiological data based on a predetermined criteria and wherein the step of communicating with said remote computer system includes transmitting the selected physiological data to said remote computer system through said cellular telephone system using said wireless data modem.

14. A method as defined in claim 9 wherein the step of communicating with said remote computer system includes transmitting at least a portion of said analysis software to said remote computer system through said cellular telephone system using said wireless data modem.

15. A method as defined in claim 9 further including the step of placing said ambulatory physiological monitor in a server mode and wherein the step of communicating with said remote computer system includes said ambulatory physiological monitor receiving commands from said remote computer system and executing said commands.

16. An ambulatory physiological monitor for recording physiological data from a patient for subsequent medical diagnosis of the patient, comprising:

a housing;

a storage device mounted in said housing for storing physiological data and analysis software;

a circuit, mounted in said housing and coupled to said storage device, for receiving a physiological signal representative of a physiological parameter of an ambulatory patient from a transducer attached to the ambulatory patient, for converting said physiological signal to said physiological data and for transferring said physiological data to said storage device, said physiological data representing the patient's condition; and a wireless data modem, mounted in said housing and coupled to said storage device, for communicating with a remote computer system as to the patient's condition by transferring said physiological data from said storage device to the remote computer system through a cellular telephone system, said wireless data modem comprising a cellular digital packet data modem for transmitting and receiving data packets.

17. An ambulatory physiological monitor as defined in claim 16 wherein said circuit includes means responsive to a predetermined event in said physiological data for initiating transmission of said physiological information to said remote computer system by said wireless data modem.

18. An ambulatory physiological monitor as defined in claim 16 wherein said storage device comprises a high capacity, miniaturized magnetic disk cartridge.

19. An ambulatory physiological monitor as defined in claim 16 wherein said circuit comprises a data buffer, an acquisition processor for converting said physiological signal to said physiological data and for storing said physiological data in said data buffer, and a command processor for transferring said physiological data from said data buffer to said storage device.

20. An ambulatory physiological monitor as defined in claim 19 wherein said command processor includes means for executing said analysis software for analyzing said physiological data.

21. An ambulatory physiological monitor as defined in claim 19 wherein said command processor includes means for controlling communication with said remote computer system with said wireless data modem.

22. An ambulatory physiological monitor as defined in claim 19 wherein said command processor includes means for responding to commands received from said remote computer system using said wireless data mode.

23. An ambulatory physiological monitor as defined in claim 19 wherein said command processor includes means for transmitting a selected portion of said physiological data to said remote computer system using said wireless data modem.

24. An ambulatory physiological monitor for recording physiological data from a patient for subsequent medical diagnosis of the patient, comprising:

a housing that is easily carried by a patient during normal activities for an extended period;

a high capacity, miniaturized magnetic disk cartridge mounted in said housing, said disk cartridge being plug connected in said monitor and being easily removable from said monitor;

an electronics module, located in said housing, for receiving a physiological signal representative of a physiological parameter of an ambulatory patient from a transducer attached to the ambulatory patient, for converting said physiological signal to physiological data and for transferring said physiological data to said disk cartridge, said physiological data representing the patient's condition;

a wireless data modem, mounted in said housing, for communicating with a remote computer system as to the patient's condition through a cellular telephone system, said wireless data modem comprising a cellular digital packet data modem for transmitting and receiving data packets; and a battery module, mounted in said housing, for supplying electrical power for operation of said disk cartridge, said electronics module and said wireless data modem.

25. An ambulatory physiological monitor as defined in claim 24 wherein said electronics module comprises a data buffer, an acquisition processor for converting said physiological signal to said physiological data and for storing said physiological data in said data buffer, and a command processor for transferring said physiological data from said data buffer to said disk cartridge when said data buffer is nearly full.

26. An ambulatory physiological monitor as defined in claim 25 wherein said disk cartridge contains analysis software and wherein said command processor includes means for executing said analysis software for analyzing said physiological data.

27. An ambulatory physiological monitor as defined in claim 24 wherein said physiological data comprises ECG data.

28. A method for recording and analyzing physiological data from a patient, comprising the steps of:

attaching an ambulatory physiological monitor containing a wireless data modem and a storage device to an ambulatory patient, said storage device having analysis software stored therein;

acquiring physiological data from the patient while the patient is ambulatory using said ambulatory physiological monitor;

storing the physiological data acquired from the patient in said storage device while the patient is ambulatory, said physiological data representing the patient's condition;

analyzing the physiological data stored in the storage device, using said analysis software, to provide physiological information; and communicating with a remote computer system as to the patient's condition through a cellular telephone system using said wireless data modem, wherein the step of communicating with said remote computer system includes transmitting said physiological information to said remote computer system, wherein the step of transmitting said physiological information to said remote computer system is executed at predetermined intervals.

29. A method for recording and analyzing physiological data from a patient, comprising the steps of:

attaching an ambulatory physiological monitor containing a wireless data modem and a storage device to an ambulatory patient, said storage device having analysis software stored therein;

acquiring physiological data from the patient while the patient is ambulatory using said ambulatory physiological monitor;

storing the physiological data acquired from the patient in said storage device while the patient is ambulatory, said physiological data representing the patient's condition;

analyzing the physiological data stored in the storage device, using said analysis software, to provide physiological information; and communicating with a remote computer system as to the patient's condition through a cellular telephone system using said wireless data modem, wherein the step of communicating with said remote computer system includes transmitting said physiological information to said remote computer system, wherein the step of transmitting said physiological information to said remote computer system is executed in response to a request from said remote computer system.

30. An ambulatory physiological monitor for recording physiological data from a patient for a subsequent medical diagnosis of the patient, comprising:

a housing;

a storage device mounted in said housing for storing physiological data and analysis software;

a circuit, mounted in said housing and coupled to said storage device, for receiving a physiological signal representative of a physiological parameter of an ambulatory patient from a transducer attached to the ambulatory patient, for converting said physiological signal to said physiological data and for transferring said physiological data to said storage device, said physiological data representing the patient's condition; and a wireless data modem, mounted in said housing and coupled to said storage device, for communicating with a remote computer system as to the patient's condition by transferring said physiological data from said storage device to the remote computer system through a cellular telephone system, wherein said circuit includes means responsive to a request by the remote computer system for initiating transmission of said physiological information to the remote computer system by said wireless data modem.

31. An ambulatory physiological monitor for recording physiological data from a patient for a subsequent medical diagnosis of the patient, comprising:

a housing;

a storage device mounted in said housing for storing physiological data and analysis software;

a circuit, mounted in said housing and coupled to said storage device, for receiving a physiological signal representative of a physiological parameter of an ambulatory patient from a transducer attached to the ambulatory patient, for converting said physiological signal to said physiological data and for transferring said physiological data to said storage device, said physiological data representing the patient's condition; and a wireless data modem, mounted in said housing and coupled to said storage device, for communicating with a remote computer system as to the patient's condition by transferring said physiological data from said storage device to the remote computer system through a cellular telephone system, wherein said circuit includes means for initiating transmission of said physiological information to the remote computer system at predetermined intervals.

32. A method for recording and analyzing physiological data from a patient, comprising the steps of:

attaching an ambulatory physiological monitor containing a storage device to an ambulatory patient;

acquiring physiological data from the patient while the patient is ambulatory using said ambulatory physiological monitor;

storing the physiological data acquired from the patient in said storage device while the patient is ambulatory;

storing analysis software in said storage device;

removing said storage device from said ambulatory physiological monitor and attaching said storage device to a computer;

transferring at least a portion of said analysis software from said storage device to said computer when said storage device is attached to said computer; and analyzing the physiological data stored in said storage device with said computer, wherein the step of analyzing the physiological data is performed with the analysis software transferred from said storage device to said computer.

33. A method for recording and analyzing physiological data from a patient, comprising the steps of:

attaching an ambulatory physiological monitor containing a wireless data modem and a storage device to an ambulatory patient;

acquiring physiological data from the patient while the patient is ambulatory using said ambulatory physiological monitor;

storing the physiological data acquired from the patient in said storage device while the patient is ambulatory;

storing analysis software in said storage device;

transferring said physiological data and at least a portion of said analysis software to a remote computer system through a cellular telephone system using said wireless data modem; and analyzing the physiological data with the remote computer with the analysis software transferred from said ambulatory physiological monitor to the remote computer system.

* * * * *